United States Patent [19]

Fujikawa et al.

[11] 4,029,490

[45] June 14, 1977

[54] METHOD OF TOBACCO SUCKER INHIBITION

[75] Inventors: Kanichi Fujikawa; Ryohei Takahashi; Isao Yokomichi; Fumio Kimura; Takeo Kaji; Nobuyuki Sakashita, all of Kusatsu, Japan

[73] Assignee: Ishihara Sangyo Kaisha Ltd., Osaka, Japan

[22] Filed: Aug. 4, 1975

[21] Appl. No.: 601,827

Related U.S. Application Data

[62] Division of Ser. No. 508,732, Sept. 24, 1974, abandoned, which is a division of Ser. No. 340,534, March 12, 1973, Pat. No. 3,883,343.

[30] Foreign Application Priority Data

Mar. 13, 1972   Japan .............................. 47-26016

[52] U.S. Cl. .................................... 71/78; 71/100; 71/103; 71/111; 71/118

[51] Int. Cl.² .......................................... A01N 9/12

[58] Field of Search .............................. 71/100, 78

[56] References Cited

UNITED STATES PATENTS 3,326,664   6/1967   Tso .......................................... 71/78
3,746,532   7/1973   Kimura et al. ...................... 71/100

OTHER PUBLICATIONS

Ichiro et al., Chem. Abst. vol. 76 (1972) 136878w.
Klingman, Chem. Abst., vol. 58 (1963) 2802f.

Primary Examiner—Elbert L. Roberts
Assistant Examiner—Catherine L. Mills
Attorney, Agent, or Firm—Oblon, Fisher, Spivak, McClelland & Maier

[57] ABSTRACT

The inhibition of the growth of tobacco plant suckers by the application to the tobacco plant of benzylthiolcarbamate having the formula,

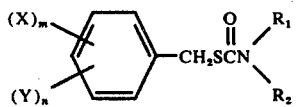

wherein
R₁ and R₂ are selected from the group consisting of acetyl, cyclohexyl, and $C_{1-6}$ alkyl group;
X and Y are selected from the group consisting of nitro, acetyl, amino,
$C_{1-3}$ alkyl
$C_{1-3}$ alkoxyl, and halogen; and
m and n are 0 or 1.

4 Claims, No Drawings

METHOD OF TOBACCO SUCKER INHIBITION

This is a division of application Ser. No. 508,732, filed Sept. 24, 1974, now abandoned, which in turn is a divisional of application Ser. No. 340,534, filed Mar. 12, 1973, now U.S. Pat. No. 3,883,343.

BACKGROUND OF THE INVENTION

1. Field of the Invention:

This invention relates to a method for inhibiting the growth of tobacco suckers. More particularly, it relates to a method for chemically treating tobacco plants to inhibit the growth of tobacco sucker.

2. Description of the Prior Art:

In the culturing of tobacco, sucker development causes a decrease in the effective yield of tobacco leaves and in the quality of the leaves. Thus, removal of the suckers from the plants is an indispensable operation. In the past, removal of the suckers by hand has been a laborious and time-consuming process. A need, therefore, exists for an effective means of chemically treating tobacco plants to inhibit the growth of tobacco suckers.

SUMMARY OF THE INVENTION

Accordingly, one object of this invention is to provide a method for inhibiting tobacco sucker without causing chemical injury to useful tobacco leaves.

This object and other objects of this invention as hereinafter will become readily apparent can be achieved by providing a method of inhibiting tobacco sucker which comprises applying benzylthiolcarbamate having the formula,

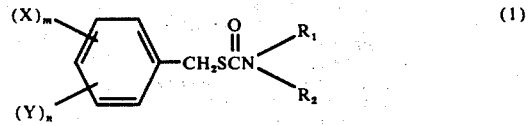

wherein
  $R_1$ and $R_2$ are $C_{1-6}$ alkyl groups, the acetyl group or the cyclohexyl group;
  X and Y are $C_{1-3}$ alkyl groups, $C_{1-3}$ alkoxy groups, the nitro group, the acetyl group, the amino group or a halogen atom;
  and $m$ and $n$ are 0 or 1, to tobacco plants.

DETAILED DESCRIPTION OF THE PREFERRED EMBODIMENTS

It is preferable in the method of this invention to apply a tobacco sucker inhibitory amount of N,N-dialkylbenzylthiolcarbamate having the formula,

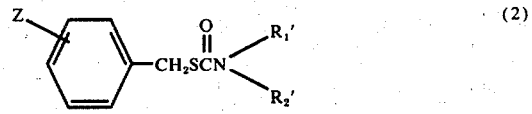

wherein
  $R_1'$ and $R_2'$ are $C_{1-6}$ alkyl groups and
  Z is a hydrogen atom, a methyl group, a chlorine atom or a fluorine atom;
to the stems and leaves of tobacco plants, preferably at the topping stage of growth of the suckers. It is especially preferably to apply a tobacco sucker inhibitory amount of a composition consisting of (A) said N,N-dialkylbenzylthiolcarbamate and (B) (a) an alkyl N-phenylcarbamate such as isopropyl N-phenylcarbamate, isopropyl N-(3-chlorophenyl) carbamate, isopropyl N-(3-methylphenyl) carbamate, and sec-butyl N-(3-methylphenyl) carbamate; or (b) a 2,6-dinitro-4-substituted aniline derivative such as N-sec-butyl-4-tert-butyl-2,6-dinitroaniline, N,N-di-n-propyl-4-trifluoromethyl-2,6-dinitroaniline and N,N-di-n-propyl-4-methylsulfonyl-2,6-dinitroaniline to the tobacco plants.

In the benzylthiolcarbamates (1) and N,N-dialkylbenzylthiolcarbamates (2), suitable $R_1$, $R_2$, $R_1'$ and $R_2'$ groups include $C_{1-6}$ alkyl groups such as methyl, ethyl, n-propyl, isopropyl, n-butyl, isobutyl, sec-butyl, tert-butyl, pentyl and hexyl, and suitable X and Y groups include $C_{1-3}$ alkyl groups such as methyl, ethyl n-propyl and isopropyl groups and $C_{1-3}$ alkoxyl groups such as methoxy, ethoxy, n-propoxy and iso-propoxy groups.

Generally, the benzylthiolcarbamate or a composition thereof is applied in the form of a solution, an emulsion or a dispersion to tobacco plants in the topping stage of growth. It is especially preferable to apply the composition to the stems and leaves near the suckers of the topped tobacco plants or the plants on which the flower buds have newly formed.

The benzylthiolcarbamates can be prepared by reacting;

1. a benzylmercaptan having the formula

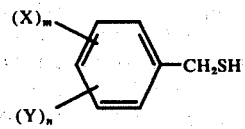

with a carbamoylhalide having the formula

wherein X, Y, $m$, $n$, $R_1$ and $R_2$ are defined as above, and $A_1$ represents a halogen atom in the presence of an alkali; or 2. a benzylthiocarbonylhalide having the formula

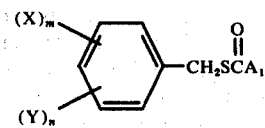

with an amine having the formula

wherein X, Y, $m$, $n$, $R_1$, $R_2$ and $A_1$ are defined as above in the presence of an alkali; or 3. a benzylhalide having the formula

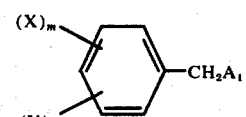

with a thiolcarbamate having the formula

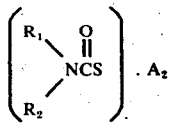

wherein X, Y, $m$, $n$, $R_1$, $R_2$ and $A_1$ are defined as above and $A_2$ represents an alkali metal, the ammonium group or a lower alkyl ammonium group.

The concentrations of the active ingredients and the amount of active ingredient used for each tobacco plant are dependent upon the varieties of tobacco, growth conditions and methods of application of the composition. When a benzylthiolcarbamate is applied to the plants without an auxiliary active ingredient, the concentrations of the active ingredient in the composition range from 100–10,000 ppm, preferably 1,000–5,000 ppm.

When N,N-dialkylbenzylthiolcarbamate is applied to the tobacco plants with an alkyl N-phenylcarbamate or a 2,6-dinitro-4-substituted aniline derivative, the concentration of each compound in the composition is in the range of 50–4,000 ppm, preferably 500–3,000 ppm.

The amounts of the aqueous composition applied to each tobacco plant is in the range of 1–100 ml, preferably 10–100 ml, especially, 20–50 ml. The ratio of the active ingredient to the auxiliary active ingredient is not limited, and it is preferably in the range of 0.05–16, especially 0.1–6 parts by weight of alkyl-N-phenylcarbamate or a 2,6-dinitro-4-substituted aniline derivative per 1 part by weight N,N-dialkylbenzylthiolcarbamate.

The compositions of this invention can be prepared by dispersing said active ingredient in water, or by admixing the active ingredient with an inert solid carrier such as talc, kaolin, bentonite, Zeeklite, starch or the like, or with an inert liquid carrier such as an alcohol, acetone, xylene, benzene, solvent naphtha, isophorone or the like. In addition, the compositions can contain a surfactant such as sodium alkylbenzenesulfonate, sodium higher alcohol sulfonate, polyoxyethylene alkylacryl ether, polyoxyethyleneglycol alkyl ether, calcium ligninesulfonate, polyvinylalcohol or the like in order to disperse the mixture in water.

When the tobacco plants are fully grown, the suckers of the plants begin to sprout. The growth of the suckers is promoted by a topping treatment, Usually, the sucker inhibitors are applied to the plants with the topping treatment. However, the sucker inhibitors can also be effectively applied to the plants during the growth of the suckers. If the active ingredient in the compositions of this invention is applied to the stems and leaves of the tobacco plants near the suckers, sprouting and growth of the suckers can be inhibited without chemical injury to the useful tobacco leaves. Thus, the application of compositions is remarkable effective for the culture of tobacco.

Having generally described this invention, a further understanding can be obtained by reference to certain specific examples which are provided herein for purposes of illustration only and are not intended to be limiting unless otherwise specified.

The following examples show some of the typical formulations of this invention and the test results from the application of the compositions to tobacco plants. These results include the sucker inhibitory effects of the compositions and the extent of chemical injury to the plants.

EXAMPLE 1

In a pot having a diameter of 15 cm, tobacco (var: Bright yellow) was cultured. When the tobacco had grown to a height of about 40 cm and had grown 7–8 nodes, the tobacco was topped. An aqueous dispersion containing 1000 ppm of an active ingredient was sprayed on the stems and leaves of the tobacco plants in quantities of 20 ml per plant. After 20 days from the date of application of the spray, the suckers were removed from the plants and collected.

The weight of the fresh suckers was measured, and the extent of chemical injury to the leaves was observed. The percent sucker inhibition was calculated by the following equation.

sucker inhibition (%) =

$$\left(1 - \frac{\text{weight of fresh sucker per plant in the treated pot}}{\text{weight of fresh sucker per plant in the untreated pot}}\right) \times 100$$

The results of the experiment are shown in Table I In the untreated pot (Control-1), water was applied instead of the dispersion of the active ingredient. In the table, the compounds used as the active ingredients are shown with their boiling points.

Table I

| Compound No. | Active ingredient | Sucker Inhibition (%) | Chemical Injury |
|---|---|---|---|
| 1 | benzyl N,N-di-n-propylthiolcarbamate | 100 | none |
| 2 | 2-methylbenzyl-N,N-di-n-propylthiolcarbamate (b.p. 158–162° C/2 mmHg) | 100 | none |
| 3 | 3-methylbenzyl-N,N-di-n-propylthiolcarbamate (b.p. 154–156° C/1.5 mmHg) | 100 | none |
| 4 | 4-methylbenzyl-N,N-di-n-propylthiolcarbamate (b.p. 147–149° C/1 mmHg) | 100 | none |
| 5 | 2-chlorobenzyl-N,N-di-n-propylthiolcarbamate (b.p. 162–165° C/2 mmHg) | 100 | none |
| 6 | 4-chlorobenzyl-N,N-di-n-propylthiolcarbamate (b.p. 163–166° C/1.5 mmHg) | 100 | none |
| 7 | 2-fluorobenzyl-N,N-di-n-propylthiolcarbamate (b.p. 154–158° C/2 mmHg) | 100 | none |
| 8 | 4-fluorobenzyl-N,N-di-n-propylthiolcarbamate (b.p. 155–160° C/2 mmHg) | 100 | none |
| 9 | 2-methyl-5-chlorobenzyl-N,N-di-n-propylthiolcarbamate | 100 | none |
| 10 | 2-methoxy-5-chlorobenzyl-N,N-di-n-propylthiolcarbamate | 100 | none |
| 11 | 2-methyl-3-bromobenzyl-N,N-di-n-propylthiolcarbamate | 100 | none |
| 12 | 4-nitrobenzyl-N,N-di-n-propylthiolcarbamate | 100 | none |
| 13 | 2-methyl-5-nitrobenzyl N,N-di-n-propylthiolcarbamate | 100 | none |
| 14 | 4-aminobenzyl-N,N-di-n-propylthiolcarbamate | 100 | none |
| 15 | 2,5-dichlorobenzyl-N,N-di-n-propylthiolcarbamate | 100 | none |
| 16 | 2,4-dimethylbenzyl-N,N-di-n-propylthiolcarbamate | 100 | none |
| 17 | 3-chloro-4-methylbenzyl-N,N-di-n-propylthiolcarbamate | 100 | none |
| 18 | 2-methoxy-5-bromobenzyl-N,N-di-n-propylthiolcarbamate | 100 | none |
| 19 | 2-ethoxy-5-chlorobenzyl-N,N-di-n-propylthiolcarbamate | 100 | none |
| 20 | 3-acetylbenzyl-N,N-di-n-propylthiolcarbamate | 100 | none |
| 21 | 2-ethoxybenzyl-N,N-dimethylthiolcarbamate | 100 | none |
| 22 | 2,5-dimethoxybenzyl-N,N- | | |

Table I-continued

| Compound No. | Active ingredient | Sucker Inhibition (%) | Chemical Injury |
|---|---|---|---|
| 23 | dimethylthiolcarbamate 2-methoxy-5-chlorobenzyl-N,N-dimethylthiolcarbamate | 100 100 | none small |
| 24 | 2-ethylbenzyl-N,N-diethyl-thiolcarbamate | 100 | none |
| 25 | benzyl N,N-diethylthiolcarbamate | 100 | none |
| 26 | 4-chlorobenzyl-N,N-diethylthiolcarbamate | 100 | none |
| 27 | benzyl N,N-di-n-butylthiolcarbamate | 100 | none |
| 28 | 2-chlorobenzyl-N,N-di-n-butylthiolcarbamate | 100 | none |
| 29 | 4-methylbenzyl-N,N-di-n-butylthiolcarbamate | 100 | none |
| 30 | 2-methyl-5-chlorobenzyl-N,N-di-iso-propylthiolcarbamate | 100 | none |
| 31 | 4-fluorobenzyl-N,N-di-iso-propylthiolcarbamate | 100 | none |
| 32 | 4-chlorobenzyl N-methyl-N-acetylthiolcarbamate | 100 | none |
| 33 | benzyl-N-ethyl-N-acetyl-thiolcarbamate | 100 | none |
| 34 | 4-chlorobenzyl-N-ethyl-N-acetylthiolcarbamate | 100 | none |
| 35 | benzyl-N-ethyl-N-cyclohexylthiolcarbamate | 100 | none |
| 36 | 2,5-dichlorobenzyl-N-ethyl-N-cyclohexylthiolcarbamate | 100 | none |
| 37 | benzyl-N-methyl-N-cyclohexylthiolcarbamate | 100 | none |
| 38 | 4-chlorobenzyl-N-methyl-N-cyclohexylthiolcarbamate | 100 | none |
| 39 | 2,5-dichlorobenzyl-N-methyl-N-cyclohexylthiolcarbamate | 100 | none |
| 40 | 2-methylbenzyl-N-methyl-N-cyclohexylthiolcarbamate | 100 | none |
| 41 | 4-methylbenzyl-N-methyl-N-cyclohexylthiolcarbamate | 100 | none |
| Cont. 1 | none | 0 | none |

EXAMPLE 2

In accordance with the method of Experiment 1 further tobacco sucker inhibition tests were conducted except that the concentration of the active ingredients in the solutions applied to the plants was 250, 500 and 2000 ppm. The results of the example are shown in Table II.

Table II

| Test No. | Active ingredient | Concentration (ppm) | sucker inhibition (%) | Chemical Injury |
|---|---|---|---|---|
| 2 - 1 | Compound 1 | 2,000 | 100 | none |
| | | 500 | 100 | " |
| | | 250 | 100 | " |
| 2 - 2 | Compound 2 | 2,000 | 100 | none |
| | | 500 | 100 | " |
| | | 250 | 100 | " |
| 2 - 3 | Compound 3 | 2,000 | 100 | none |
| | | 500 | 100 | " |
| | | 250 | 100 | " |
| 2 - 4 | Compound 4 | 2,000 | 100 | none |
| | | 500 | 100 | " |
| | | 250 | 100 | " |
| 2 - 5 | Compound 5 | 2,000 | 100 | none |
| | | 500 | 100 | " |
| | | 250 | 100 | " |
| 2 - 6 | Compound 6 | 2,000 | 100 | none |
| | | 500 | 100 | " |
| | | 250 | 100 | " |
| 2 - 7 | Compound 7 | 2,000 | 100 | none |
| | | 500 | 100 | " |
| | | 250 | 100 | " |
| 2 - 8 | Compound 8 | 2,000 | 100 | none |
| | | 500 | 100 | " |
| | | 250 | 100 | " |
| 2 - 9 | Compound 9 | 2,000 | 100 | small |
| | | 500 | 100 | none |
| | | 250 | 100 | " |
| Control 1 | — | — | 0 | none |

EXAMPLE 3

In a pot having a diameter of 15 cm, a tobacco (var: Bright yellow) was cultured.

When the tobacco had grown to a height of about 1 m when 20–25 nodes had grown, and when from one to two flower buds had bloomed, the tobacco was topped.

When the suckers had grown to a length of to 2–3 cm after 7 days from topping, various concentrations of each active ingredient in aqueous dispersions were sprayed onto the stems and leaves of tobacco plants in quantities of 20 ml per plant.

In a comparative test, (Control-2), a 58% aqueous dispersion of the diethanolamine salt of maleic hydrazide was sprayed onto the stems and leaves of tobacco plants. Twenty days after the day of application, the percent of sucker inhibition and the extent of chemical injury were measured in accordance with the method of Experiment 1. The results are shown in Table III. The concentration of Test Nos. 3–10 is in terms of maleic hydrazide in Table III.

Table III

| Test No. | Active ingredient | Concentration (ppm) | sucker inhibition (%) | Chemical injury |
|---|---|---|---|---|
| 3 - 1 | Compound 1 | 4,000 | 100 | none |
| | | 2,000 | 100 | " |
| | | 1,000 | 100 | " |
| | | 500 | 100 | " |
| 3 - 2 | Compound 2 | 4,000 | 100 | none |
| | | 2,000 | 100 | " |
| | | 1,000 | 100 | " |
| | | 500 | 100 | " |
| 3 - 3 | Compound 3 | 4,000 | 100 | small |
| | | 2,000 | 100 | small |
| | | 1,000 | 100 | none |
| | | 500 | 100 | " |
| 3 - 4 | Compound 4 | 4,000 | 100 | none |
| | | 2,000 | 100 | " |
| | | 1,000 | 100 | " |
| | | 500 | 100 | " |
| 3 - 5 | Compound 5 | 4,000 | 100 | none |
| | | 2,000 | 100 | " |
| | | 1,000 | 100 | " |
| | | 500 | 100 | " |
| 3 - 6 | Compound 6 | 4,000 | 100 | none |
| | | 2,000 | 100 | " |
| | | 1,000 | 100 | " |
| | | 500 | 100 | " |
| 3 - 7 | Compound 7 | 4,000 | 100 | none |
| | | 2,000 | 100 | " |
| | | 1,000 | 100 | " |
| | | 500 | 100 | " |
| 3 - 8 | Compound 8 | 4,000 | 100 | none |
| | | 2,000 | 100 | " |
| | | 1,000 | 100 | " |
| | | 500 | 100 | " |
| 3 - 9 | Compound 9 | 4,000 | 100 | none |
| | | 2,000 | 100 | " |
| | | 1,000 | 100 | " |
| | | 500 | 100 | " |
| 3 - 10 | Control 2 maleic hydrazide | 4,000 | 69 | small |
| | | 2,000 | 41 | none |
| | | 1,000 | 51 | " |
| Control 1 | none | — | 0 | none |

EXAMPLE 4

In a pot of 1/2000 are (1/81000 acre) on a wet field, tobacco (var: Bright yellow) was cultured.

When the tobacco had grown to a height of about 1 m, and when the flower buds had just begun to bloom, the tobacco was topped. This tobacco was used for the tests.

The tobacco was planted in quantities of 1 plant per pot, and the tests were conducted twice. The active ingredients and the auxiliary active ingredients were formulated as follows:

1. Active ingredient - N,N-dialkylbenzylthiolcarbamate:
   a. 20 parts by weight N,N-dialkylbenzylthiolcarbamate
   b. 70 parts by weight xylene, and
   c. 10 parts by weight polyoxyethylene laurylether
   were mixed and the mixture was emulsified for each of the desired concentration;

2. Auxiliary active ingredient: an alkyl-N-phenylcarbamate or a 4-substituted aniline derivative.

An emulsion of the auxiliary active ingredient was prepared in accordance with the method shown above except that N,N-dialkylbenzylthiolcarbamate was replaced with an alkyl-N-phenylcarbamate or a 2,6-dinitro-4-substituted aniline derivative.

In order to test the differences in effectiveness between the active ingredients of this invention, and especially the special effectiveness of the compositions containing the active ingredient and the auxiliary active ingredient, the sucker inhibition percentage was measured 50 days after the date of application of sprays containing the compositions indicated. The results are shown in Tables IV–X.

Table IV

| Test No. | Active ingredient | concentration (ppm) | Auxiliary active ingredient | concentration (ppm) | Sucker inhibition (%) |
|---|---|---|---|---|---|
| Control 1 | — | 0 | — | 0 | 0 |
| Control 2 | | | maleic hydrazide | 4000 | 95 |
| | | | | 2000 | 63 |
| | | | | 1000 | 25 |
| 4 - 0 | | 0 | Isopropyl-N-(3-chlorophenyl)carbamate | 4000 | 69 |
| | | | | 2000 | 53 |
| | | | | 1000 | 41 |
| 4 - 1 | Compound 1 | 4,000 | | 0 | 75 |
| | | 2,000 | " | 1000 | 100 |
| | | 1,000 | | 1000 | 100 |
| | | 500 | | 1000 | 100 |
| 4 - 2 | Compound 2 | 4,000 | | 0 | 84 |
| | | 2,000 | | 1000 | 100 |
| | | 1,000 | " | 1000 | 100 |
| | | 500 | | 1000 | 100 |
| 4 - 3 | Compound 3 | 4,000 | | 0 | 81 |
| | | 2,000 | | 1000 | 100 |
| | | 1,000 | " | 1000 | 100 |
| | | 500 | | 1000 | 100 |
| 4 - 4 | Compound 4 | 4,000 | | 0 | 73 |
| | | 2,000 | | 1000 | 100 |
| | | 1,000 | " | 1000 | 100 |
| | | 500 | | 1000 | 100 |
| 4 - 5 | Compound 5 | 4,000 | | 0 | 82 |
| | | 2,000 | | 1000 | 100 |
| | | 1,000 | " | 1000 | 100 |
| | | 500 | | 1000 | 100 |
| 4 - 6 | Compound 6 | 4,000 | | 0 | 84 |
| | | 2,000 | | 1000 | 100 |
| | | 1,000 | " | 1000 | 100 |
| | | 500 | | 1000 | 100 |
| 4 - 7 | Compound 7 | 4,000 | | 0 | 78 |
| | | 2,000 | | 1000 | 100 |
| | | 1,000 | " | 1000 | 100 |
| | | 500 | | 1000 | 100 |
| 4 - 8 | Compound 8 | 4,000 | | 0 | 77 |
| | | 2,000 | | 1000 | 100 |
| | | 1,000 | " | 1000 | 100 |
| | | 500 | | 1000 | 100 |

Table V

| Test No. | Active ingredient | Concentration (ppm) | Auxiliary active ingredient | Concentration (ppm) | Sucker inhibition (%) |
|---|---|---|---|---|---|
| 5 - 0 | | 0 | Isopropyl N-phenylcarbamate | 4,000 | 46 |
| | | | | 2,000 | 31 |
| | | | | 1,000 | 18 |
| 5 - 1 | Compound 1 | 2,000 | | 1,000 | 100 |
| | | 1,000 | " | 1,000 | 100 |
| | | 500 | | 1,000 | 91 |
| 5 - 2 | Compound 2 | 2,000 | | 1,000 | 100 |
| | | 1,000 | " | 1,000 | 100 |
| | | 500 | | 1,000 | 94 |
| 5 - 3 | Compound 3 | 2,000 | | 1,000 | 100 |
| | | 1,000 | " | 1,000 | 100 |
| | | 500 | | 1,000 | 88 |
| 5 - 4 | Compound 4 | 2,000 | | 1,000 | 98 |
| | | 1,000 | " | 1,000 | 94 |
| | | 500 | | 1,000 | 72 |
| 5 - 5 | Compound 5 | 2,000 | | 1,000 | 100 |
| | | 1,000 | " | 1,000 | 100 |
| | | 500 | | 1,000 | 92 |
| 5 - 6 | Compound 6 | 2,000 | | 1,000 | 100 |

Table V-continued

| Test No. | Active ingredient | Concentration (ppm) | Auxiliary active ingredient | Concentration (ppm) | Sucker inhibition (%) |
|---|---|---|---|---|---|
| | | 1,000 | " | 1,000 | 92 |
| | | 500 | | 1,000 | 85 |
| 5 - 7 | Compound 7 | 2,000 | | 1,000 | 100 |
| | | 1,000 | " | 1,000 | 100 |
| | | 500 | | 1,000 | 90 |
| 5 - 8 | Compound 8 | 2,000 | | 1,000 | 93 |
| | | 1,000 | " | 1,000 | 87 |
| | | 500 | | 1,000 | 75 |

Table VI

| Test No. | Active ingredient | Concentration (ppm) | Auxiliary active ingredient | Concentration (ppm) | sucker inhibition (%) |
|---|---|---|---|---|---|
| 6 - 0 | | 0 | Isopropyl N-(3-methylphenyl) carbamate | 4,000 | 72 |
| | | | | 2,000 | 56 |
| | | | | 1,000 | 43 |
| 6 - 1 | Compound 1 | 2,000 | " | 1,000 | 100 |
| | | 1,000 | | 1,000 | 100 |
| | | 500 | | 1,000 | 96 |
| 6 - 2 | Compound 2 | 2,000 | " | 1,000 | 100 |
| | | 1,000 | | 1,000 | 100 |
| | | 500 | | 1,000 | 100 |
| 6 - 3 | Compound 3 | 2,000 | " | 1,000 | 100 |
| | | 1,000 | | 1,000 | 100 |
| | | 500 | | 1,000 | 100 |
| 6 - 4 | Compound 4 | 2,000 | " | 1,000 | 100 |
| | | 1,000 | | 1,000 | 100 |
| | | 500 | | 1,000 | 95 |
| 6 - 5 | Compound 5 | 2,000 | " | 1,000 | 100 |
| | | 1,000 | | 1,000 | 100 |
| | | 500 | | 1,000 | 100 |
| 6 - 6 | Compound 6 | 2,000 | " | 1,000 | 100 |
| | | 1,000 | | 1,000 | 100 |
| | | 500 | | 1,000 | 100 |
| 6 - 7 | Compound 7 | 2,000 | " | 1,000 | 100 |
| | | 1,000 | | 1,000 | 100 |
| | | 500 | | 1,000 | 100 |
| 6 - 8 | Compound 8 | 2,000 | " | 1,000 | 100 |
| | | 1,000 | | 1,000 | 100 |
| | | 500 | | 1,000 | 89 |

Table VII

| Test No. | Active ingredient | Concentration (ppm) | Auxiliary active ingredient | Concentration (ppm) | sucker inhibition (%) |
|---|---|---|---|---|---|
| 7 - 0 | | 0 | sec-butyl N-(3-methylphenyl) carbamate | 4,000 | 66 |
| | | | | 2,000 | 44 |
| | | | | 1,000 | 28 |
| 7 - 1 | Compound 1 | 2,000 | " | 1,000 | 100 |
| | | 1,000 | | 1,000 | 100 |
| | | 500 | | 1,000 | 98 |
| 7 - 2 | Compound 2 | 2,000 | " | 1,000 | 100 |
| | | 1,000 | | 1,000 | 100 |
| | | 500 | | 1,000 | 98 |
| 7 - 3 | Compound 3 | 2,000 | " | 1,000 | 100 |
| | | 1,000 | | 1,000 | 100 |
| | | 500 | | 1,000 | 92 |
| 7 - 4 | Compound 4 | 2,000 | " | 1,000 | 100 |
| | | 1,000 | | 1,000 | 100 |
| | | 500 | | 1,000 | 88 |
| 7 - 5 | Compound 5 | 2,000 | " | 1,000 | 100 |
| | | 1,000 | | 1,000 | 100 |
| | | 500 | | 1,000 | 96 |
| 7 - 6 | Compound 6 | 2,000 | " | 1,000 | 100 |
| | | 1,000 | | 1,000 | 96 |
| | | 500 | | 1,000 | 97 |
| 7 - 7 | Compound 7 | 2,000 | " | 1,000 | 100 |
| | | 1,000 | | 1,000 | 100 |
| | | 500 | | 1,000 | 89 |
| 7 - 8 | Compound 8 | 2,000 | " | 1,000 | 100 |
| | | 1,000 | | 1,000 | 91 |
| | | 500 | | 1,000 | 87 |

Table VIII

| Test No. | Active ingredient | Concentration (ppm) | Auxiliary active ingredient | Concentration (ppm) | sucker inhibition |
|---|---|---|---|---|---|
| 8 - 0 | | 0 | N-sec-butyl-4-tert-butyl 2,6-dinitro-aniline | 4,000 | 68 |
| | | | | 2,000 | 56 |
| | | | | 1,000 | 52 |
| 8 - 1 | Compound 1 | 2,000 | " | 1,000 | 100 |
| | | 1,000 | | 1,000 | 100 |
| | | 500 | | 1,000 | 100 |
| 8 - 2 | Compound 2 | 2,000 | " | 1,000 | 100 |
| | | 1,000 | | 1,000 | 100 |
| | | 500 | | 1,000 | 100 |
| 8 - 3 | Compound 3 | 2,000 | " | 1,000 | 100 |
| | | 1,000 | | 1,000 | 100 |
| | | 500 | | 1,000 | 100 |
| 8 - 4 | Compound 4 | 2,000 | " | 1,000 | 100 |
| | | 1,000 | | 1,000 | 100 |

Table VIII-continued

| Test No. | Active ingredient | Concentration (ppm) | Auxiliary active ingredient | Concentration (ppm) | sucker inhibition |
|---|---|---|---|---|---|
|  |  | 500 |  | 1,000 | 98 |
| 8 - 5 | Compound 5 | 2,000 |  | 1,000 | 100 |
|  |  | 1,000 | " | 1,000 | 100 |
|  |  | 500 |  | 1,000 | 100 |
| 8 - 6 | Compound 6 | 2,000 |  | 1,000 | 100 |
|  |  | 1,000 | " | 1,000 | 100 |
|  |  | 500 |  | 1,000 | 100 |
| 8 - 7 | Compound 7 | 2,000 |  | 1,000 | 100 |
|  |  | 1,000 | " | 1,000 | 100 |
|  |  | 500 |  | 1,000 | 100 |
| 8 - 8 | Compound 8 | 2,000 |  | 1,000 | 100 |
|  |  | 1,000 | " | 1,000 | 100 |
|  |  | 500 |  | 1,000 | 100 |

Table IX

| Test No. | Active ingredient | Concentration (ppm) | Auxiliary active ingredient | Concentration (ppm) | sucker inhibition (%) |
|---|---|---|---|---|---|
| 9 - 0 |  |  | N,N-di-n-propyl 4-trifluoromethyl 2,6-dinitro-aniline | 4,000 | 52 |
|  |  |  |  | 2,000 | 31 |
|  |  |  |  | 1,000 | 11 |
| 9 - 1 | Compound 1 | 2,000 |  | 1,000 | 100 |
|  |  | 1,000 | " | 1,000 | 88 |
|  |  | 500 |  | 1,000 | 75 |
| 9 - 2 | Compound 2 | 2,000 |  | 1,000 | 100 |
|  |  | 1,000 | " | 1,000 | 90 |
|  |  | 500 |  | 1,000 | 86 |
| 9 - 3 | Compound 3 | 2,000 |  | 1,000 | 100 |
|  |  | 1,000 | " | 1,000 | 86 |
|  |  | 500 |  | 1,000 | 74 |
| 9 - 4 | Compound 4 | 2,000 |  | 1,000 | 100 |
|  |  | 1,000 | " | 1,000 | 75 |
|  |  | 500 |  | 1,000 | 60 |
| 9 - 5 | Compound 5 | 2,000 |  | 1,000 | 100 |
|  |  | 1,000 | " | 1,000 | 92 |
|  |  | 500 |  | 1,000 | 84 |
| 9 - 6 | Compound 6 | 2,000 |  | 1,000 | 100 |
|  |  | 1,000 | " | 1,000 | 85 |
|  |  | 500 |  | 1,000 | 71 |
| 9 - 7 | Compound 7 | 2,000 |  | 1,000 | 100 |
|  |  | 1,000 | " | 1,000 | 85 |
|  |  | 500 |  | 1,000 | 76 |
| 9 - 8 | Compound 8 | 2,000 |  | 1,000 | 92 |
|  |  | 1,000 | " | 1,000 | 88 |
|  |  | 500 |  | 1,000 | 72 |

Table X

| Test No. | Active ingredient | Concentration (ppm) | Auxiliary active ingredient | Concentration (ppm) | sucker inhibition (%) |
|---|---|---|---|---|---|
| 10 - 0 |  | 0 | N,N-di-n-propyl 4-methylsulfonyl-2,6-dinitro-aniline | 4,000 | 49 |
|  |  |  |  | 2,000 | 26 |
|  |  |  |  | 1,000 | 12 |
| 10 - 1 | Compound 1 | 2,000 |  | 1,000 | 96 |
|  |  | 1,000 | " | 1,000 | 88 |
|  |  | 500 |  | 1,000 | 66 |
| 10 - 2 | Compound 2 | 2,000 |  | 1,000 | 92 |
|  |  | 1,000 | " | 1,000 | 78 |
|  |  | 500 |  | 1,000 | 72 |
| 10 - 3 | Compound 3 | 2,000 |  | 1,000 | 91 |
|  |  | 1,000 | " | 1,000 | 76 |
|  |  | 500 |  | 1,000 | 60 |
| 10 - 4 | Compound 4 | 2,000 |  | 1,000 | 96 |
|  |  | 1,000 | " | 1,000 | 81 |
|  |  | 500 |  | 1,000 | 71 |
| 10 - 5 | Compound 5 | 2,000 |  | 1,000 | 91 |
|  |  | 1,000 | " | 1,000 | 77 |
|  |  | 500 |  | 1,000 | 71 |
| 10 - 6 | Compound 6 | 2,000 |  | 1,000 | 100 |
|  |  | 1,000 | " | 1,000 | 82 |
|  |  | 500 |  | 1,000 | 65 |
| 10 - 7 | Compound 7 | 2,000 |  | 1,000 | 90 |
|  |  | 1,000 | " | 1,000 | 82 |
|  |  | 500 |  | 1,000 | 79 |
| 10 - 8 | Compound 8 | 2,000 |  | 1,000 | 88 |
|  |  | 1,000 | " | 1,000 | 72 |
|  |  | 500 |  | 1,000 | 61 |

According to the test results, the active benzylthiolcarbamate ingredients of this invention exhibit a remarkable inhibitory effect on the growth of tobacco suckers compared to other sucker inhibitors such as maleic hydrazide. At the same time very little chemical injury is observed on the treated tobacco leaves.

In the instances when an auxiliary active ingredient such as an alkyl-N-phenylcarbamate or a 2,6-dinitro-4-substituted aniline derivative was blended with an N,N-dialkylbenzylthiolcarbamate for the treatment of tobacco suckers, the blend of ingredients exhibited a remarkable synergistic effect in the treatment of the plants. Inhibition of tobacco sucker for those plants treated with this blend was maintained for a substantially longer period of time than for those plants treated with a single active ingredient or maleic hydrazide.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A plant growth inhibiting composition which comprises the combination of a benzylthiolcarbamate having the formula

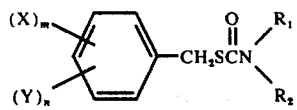

wherein
 $R_1$ and $R_2$ are selected from the group consisting of acetyl, cyclohexyl, and $C_{1-6}$ alkyl groups,
 X and Y are selected from the group consisting of nitro, acetyl, amino, $C_{1-3}$ alkyl, $C_{1-3}$ alkoxyl and halogen; and
 $m$ and $n$ are 0 or 1 with an alkyl-N-phenylcarbamate, wherein the phenyl ring is unsubstituted or substituted with a lower alkyl group or a halogen atom; and
 wherein said carbamate is mixed with said benzylthiolcarbamate in a ratio of from 0.1 to 6:1.

2. The composition of claim 1, wherein said alkyl-N-phenyl-carbamate is isopropyl n-phenylcarbamate, isopropyl N-(3-chlorophenyl) carbamate, isopropyl N-(3-methylphenyl)carbamate or sec-butyl N-(3-methylphenyl)carbamate.

3. A method of inhibiting the growth of suckers of tobacco plants which comprises applying to the tobacco plant an effective amount of a composition which comprises the combination of a benzylthiolcarbamate having the formula

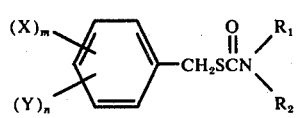

wherein
 $R_1$ and $R_2$ are selected from the group consisting of acetyl, cyclohexyl, and $C_{1-6}$ alkyl groups.
 X and Y are selected from the group consisting of nitro, acetyl, amino, $C_{1-3}$ alkyl and halogen; and
 $m$ and $n$ are 0 or 1, with an alkyl-N-phenylcarbamate; wherein the phenyl ring is unsubstituted or substituted with a lower alkyl group or a halogen atom; and
 wherein said carbamate is mixed with said benzylthiolcarbamate in a ratio of from 0.05 to 16:1.

4. The method of claim 3, wherein said alkyl-N-phenylcarbamate is isopropyl n-phenylcarbamate, isopropyl N-(3-chlorophenyl) carbamate, isopropyl N-(3-methylphenyl) carbamate or sec-butyl N-(3-methylphenyl) carbamate.

* * * * *